United States Patent
Mases

[11] Patent Number: 5,191,468
[45] Date of Patent: Mar. 2, 1993

[54] WELDER'S HELMET

[75] Inventor: Kjell Mases, Gagnef, Sweden

[73] Assignee: Hornell Elektrooptik AB, Gagnef, Sweden

[21] Appl. No.: 776,398

[22] PCT Filed: Jun. 5, 1990

[86] PCT No.: PCT/SE90/00387
§ 371 Date: Nov. 21, 1991
§ 102(e) Date: Nov. 21, 1991

[87] PCT Pub. No.: WO90/14809
PCT Pub. Date: Dec. 13, 1990

[30] Foreign Application Priority Data
Jun. 5, 1989 [SE] Sweden ................. 8902039

[51] Int. Cl.⁵ .............................. G02B 5/22
[52] U.S. Cl. .................... 359/361; 359/350; 359/892; 2/12; 2/15; 219/147
[58] Field of Search ........... 359/84, 85, 350, 361, 359/885, 892; 219/147; 2/8, 12, 15

[56] References Cited

U.S. PATENT DOCUMENTS

| Re. 29,684 | 6/1978 | Gordon | 219/147 |
| 3,756,692 | 9/1973 | Scott | 219/147 |
| 3,868,727 | 3/1975 | Paschall | |
| 4,039,254 | 8/1977 | Harsch | 2/8 |
| 4,707,860 | 11/1987 | Holmstrom | |
| 4,863,244 | 9/1989 | Fuerthbauer et al. | 2/8 |

FOREIGN PATENT DOCUMENTS 425048 8/1982 Sweden.
445969 8/1986 Sweden.

Primary Examiner—Bruce Y. Arnold
Assistant Examiner—J. P. Ryan
Attorney, Agent, or Firm—Young & Thompson

[57] ABSTRACT

A welder's helmet (1) provided with a fast filter (3) which is controlled by welding light and through which the wearer of the helmet can see clearly in the absence of welding light. In accordance with the invention, the helmet is complemented with side windows (4) operative to filter out IR and UV radiation and having a moderate filter effect for visible light.

2 Claims, 1 Drawing Sheet

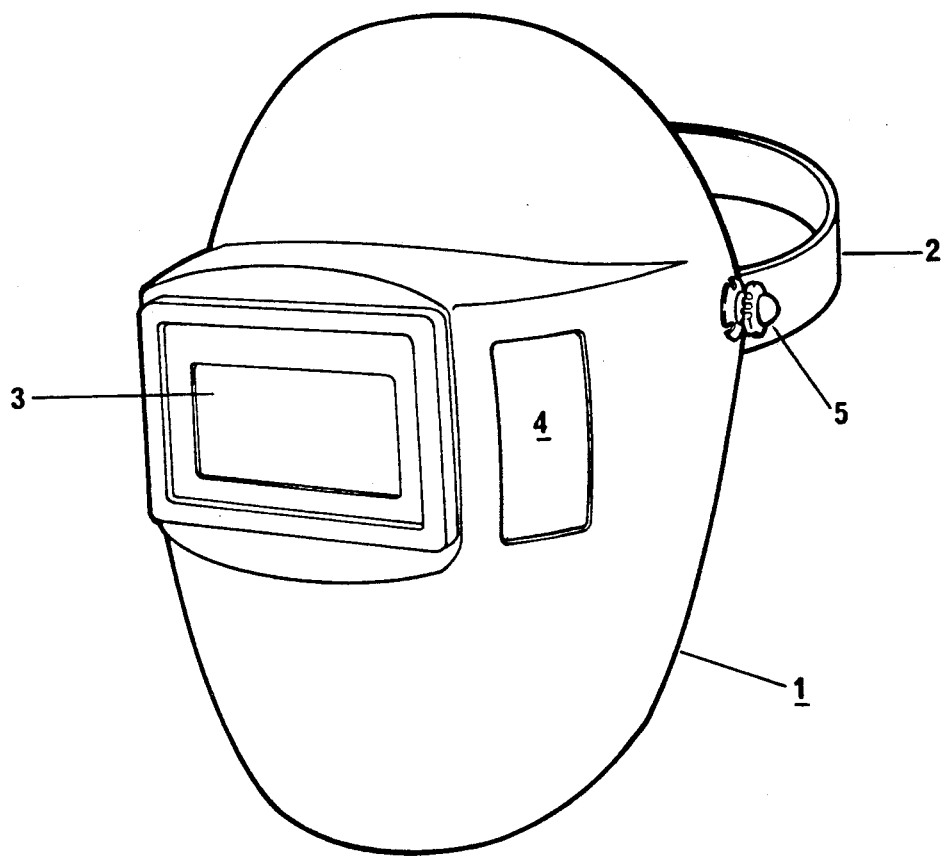

WELDER'S HELMET

The present invention relates to welder's helmets of the kind which are fitted with so-called fast filters, i.e. a light filter which remains comparatively clear until subjected to the effect of welding light, whereupon the filter darkens, normally through switching of the polarization of one or more liquid crystal layers in combination with polarizing filters.

Helmets that are fitted with permanent filters are used solely during an actual welding operation, and when no welding is in progress, the filters, and possible also parts of the helmet, are moved out of the way. Welder's helmets fitted with so-called fast filters, however, are normally worn constantly during work and may often be provided, comfortably, with "air conditioning" and perhaps also with earphones or hearing protectors, these facilities being appreciated in some industrial environments.

One drawback with helmets of this kind is that because the wearer can only see straight ahead through the fast filter, he loses the comprehension of space. Many workmen find this uncomfortable and the lowered perception may result in an accident or injury.

An object of the invention is to provide an improvement in this regard. This object is achieved in accordance with the invention with a welder's helmet having the characteristic features set forth in claim 1.

Thus, according to the invention, separate filter windows are disposed on respective sides of the fast filter. These windows will preferably have a given filter factor, in order to give equilibrium and freedom from dazzle. The welding light generated will result in significant illumination of the surroundings, as will also the light generated by other welding operations, particularly in workshops in which several welders are at work. Accordingly, the filter windows will preferably have a given filter effect in the visible range and will also preferably give low transmission in the UV-range and in the IR-range.

Known to the art are welder's helmets that are fitted with conventional filter glass and which have a large, integrated front window. This front window has a higher density in the center thereof, so as to protect the wearer against welding light which falls immediately on the eyes, and a lower density at the sides of the window. One problem with a helmet construction of this kind is that direct welding light will enter the helmet and illuminate the face of the wearer, such that the face becomes suffused with light within the helmet. The illuminated face of the wearer of the helmet is reflected in the rear side of the filter part of higher density, therewith decreasing the contrast. Furthermore, the general brightness to which the eyes are subjected causes the eyes to adjust to an excessively high light density. When the welding operation has been completed, it takes time for the eyes to adjust to the reduced brightness. An object of the invention is to improve the field of vision, without suffering these drawbacks.

BRIEF DESCRIPTION OF THE DRAWING

The invention will now be described in more detail with reference to an exemplifying embodiment thereof and with reference to the accompanying drawing, which illustrates a welder's helmet.

DETAILED DESCRIPTION OF THE INVENTION

The welder's helmet 1 illustrated in the drawing comprises a curved, plastic face mask. The helmet further comprises a head strap 2 which is tightened around the head of the wearer, so as to support the helmet. The face mask is pivotally attached to the head strap at two points thereon, one of said points being referenced 5 in the drawing while the other point on the other side of the face mask is not visible in the drawing. The face mask can thus be pivoted about these pivot attachments, so as to enable the mask to be raised and leave the face free.

The helmet further includes a framed welding glass 3 which is mounted opposite the position of the wearer's eyes. This glass is of the fast-filter type and may be a filter glass of the kind marketed by us under the trademark "Speedglas", which comprises in sequence an interference filter which will solely allow visible light to pass through and a combination of polarization filters and liquid crystal layers controlled by a light sensor (not shown) so as to darken the glass quickly upon the occurrence of welding light, as described in SE-A-7804630-7.

The face mask has provided on respective sides of the welding glass 3 side openings in which side filters 4 are fitted. These side filters are operative to filter-out IR and UV radiation and have a visual filter effect of, e.g., between 4 and 5 degrees of density.

The degree of density is defined conventionally as $$D = 1 + \frac{7}{3} \frac{10}{\log} \frac{1}{T}$$

where T is the relative transmission.

Since the glass light filters are of conventional design, they may be manufactured as curved so as to conform to the curved shape of the face mask 1. It is important that the filters are oriented and positioned so that light from the weld source will not enter directly from the front, but solely from radiation spread to the surroundings from the welding light source, and dampened so that the helmet interior will not become too illuminated.

The inventive helmet can be combined with different kinds of known devices, such as air-exchange devices, with or without air filters, earphones, etc., and as a result of the provision of side windows, the helmet will be far more comfortable to the wearer than a helmet which solely includes the central window glass. The inventive helmet can thus be worn advantageously over long periods without causing discomfort, even by workmen who would otherwise feel discomfort when wearing such helmets and who might even suffer psychological problems of a light claustrophobic nature. The inventive welder's helmet may also be combined with a protective helmet of the kind which covers the head, so as to protect the head against injury from mechanical sources.

I claim:

1. A welder's helmet comprising a front surface and opposite side surfaces, and provided on said front surface with at least one so-called fast filter which assumes an increased optical density in response to welding light incident thereon, each of said opposite side surfaces being provided with separate side windows fitted with filters which will essentially exclude IR-radiation and UV-radiation and have a predetermined constant filter effect for visible light, said front surface being free of transparent regions other than said at least one fast filter.

2. A welder's helmet according to claim 1, characterized in that the filter effect of the filters in the respective side windows has a degree of density of 4–5.

* * * * *